(12) United States Patent
Hanis et al.

(10) Patent No.: US 9,721,446 B1
(45) Date of Patent: Aug. 1, 2017

(54) DETECTING ALLERGENS PRESENT IN A PRODUCT

(71) Applicant: International Business Machines Corporation, Armonk, NY (US)

(72) Inventors: Thomas T. Hanis, Raleigh, NC (US); Bruce H. Hyre, Cary, NC (US); Jessica G. Smith, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/211,911

(22) Filed: Jul. 15, 2016

(51) Int. Cl.
*G08B 21/18* (2006.01)
(52) U.S. Cl.
CPC ..................... *G08B 21/18* (2013.01)
(58) Field of Classification Search
CPC .......... G08B 3/10; G08B 21/18; G08B 21/22; G06K 7/0008; G06K 19/07749; G06Q 30/06; G06Q 30/02; G06Q 30/0623
USPC .......... 340/540, 10.1, 572.1, 573.1; 235/383, 235/375, 492; 705/26.16
See application file for complete search history.

(56) References Cited

U.S. PATENT DOCUMENTS

| | | | | |
|---|---|---|---|---|
| 5,478,989 | A * | 12/1995 | Shepley | G06Q 20/343 235/375 |
| 6,375,077 | B1 | 4/2002 | Hankins | |
| 6,652,455 | B1 * | 11/2003 | Kocher | G06F 19/322 128/921 |
| 6,796,507 | B2 | 9/2004 | Bean et al. | |
| 7,617,132 | B2 | 11/2009 | Reade et al. | |
| 7,953,873 | B1 | 5/2011 | Madurzak | |
| 7,999,674 | B2 * | 8/2011 | Kamen | A61M 5/14244 340/572.1 |
| 8,746,576 | B2 | 6/2014 | Baym et al. | |
| 8,810,417 | B2 * | 8/2014 | Hood | G01N 33/14 340/603 |

(Continued)

FOREIGN PATENT DOCUMENTS

| | | |
|---|---|---|
| MX | PA03008780 A | 5/2004 |
| WO | 2008031163 A1 | 3/2008 |

OTHER PUBLICATIONS

Voordouw et al., "The Main Problems of Food Allergic Consumers Concerning Food Labeling: an Ethnographic Study," 98th EAAE Seminar 'Marketing Dynamics within the Global Trading System: New Perpsectives', Chania, Crete, Greece, Jun. 29-Jul. 2, 2006, pp. 1-15, see p. 13, paragraph 5-p. 14.

*Primary Examiner* — George Bugg
*Assistant Examiner* — Munear Akki
(74) *Attorney, Agent, or Firm* — Robert A. Voigt, Jr.; Winstead, P.C.

(57) ABSTRACT

A method, system and computer program product for detecting allergens present in a product. A tag (e.g., passive RFID tag) receives a query from the user of a computing device containing a list of allergens to determine if an allergen is present in the product (e.g., product for ingestion). Product information associated with the product in stored in secure memory (e.g., write-only memory) on the tag. The tag determines if an allergen to the user is present in the product using the list of allergens in the query as well as the product information associated with the product. The tag then notifies the user of the computing device regarding whether an allergen to the user is present in the product based on the determination. In this manner, allergens are detected in a product and made known to the user.

20 Claims, 3 Drawing Sheets

(56) References Cited

U.S. PATENT DOCUMENTS

| | | | |
|---|---|---|---|
| 9,072,317 B2 | 7/2015 | Minvielle | |
| 9,529,385 B2 * | 12/2016 | Connor | G09B 19/0092 |
| 2001/0028308 A1 * | 10/2001 | De La Huerga | A61M 5/14212 340/573.1 |
| 2002/0139846 A1 * | 10/2002 | Needham | G06Q 30/06 235/383 |
| 2004/0078218 A1 * | 4/2004 | Badinelli | G06F 19/324 705/2 |
| 2004/0100380 A1 * | 5/2004 | Lindsay | G06K 19/0717 340/540 |
| 2005/0091124 A1 | 4/2005 | White | |
| 2008/0005082 A1 * | 1/2008 | Hughes | G06F 19/3475 |
| 2012/0253828 A1 | 10/2012 | Bellacicco, Jr. | |
| 2012/0286959 A1 * | 11/2012 | Ray | G08B 21/043 340/627 |
| 2013/0049932 A1 * | 2/2013 | Baym | A23L 35/00 340/10.1 |
| 2013/0049933 A1 * | 2/2013 | Baym | G06K 19/0723 340/10.1 |
| 2015/0100516 A1 | 4/2015 | Hicks et al. | |

* cited by examiner

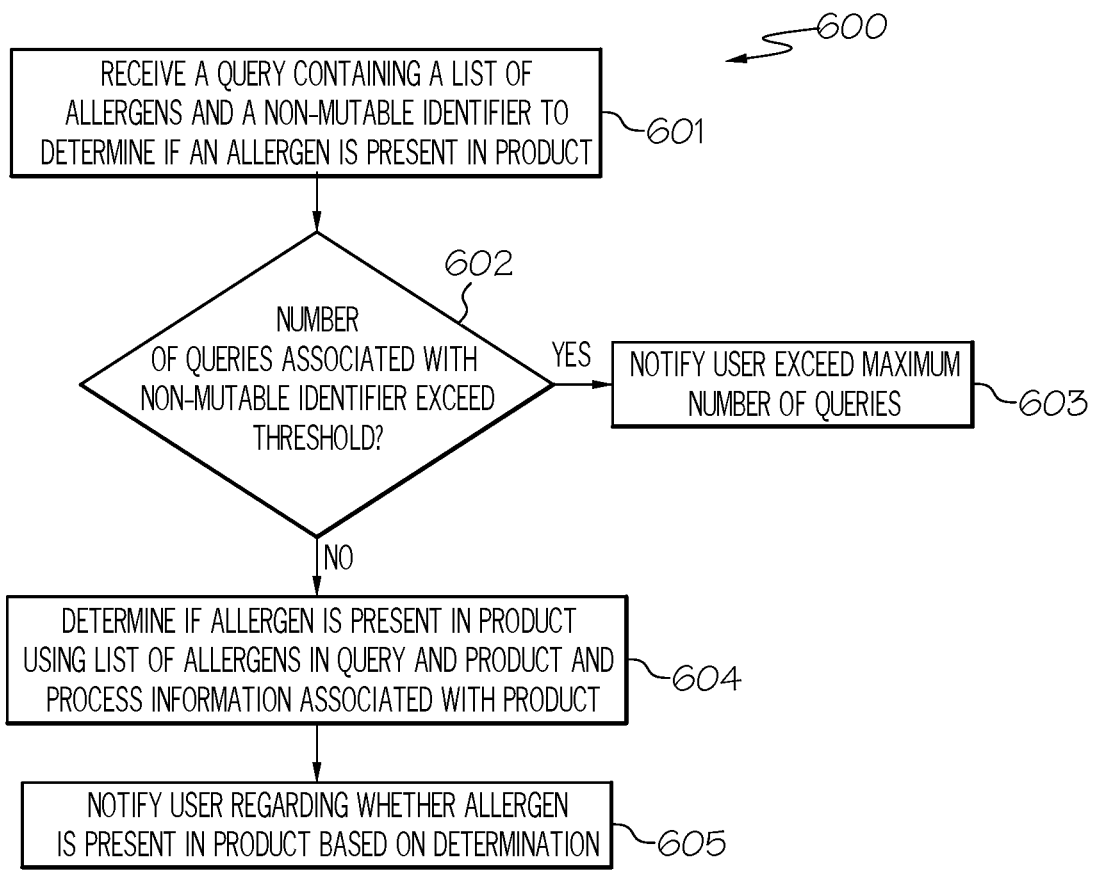

DETECTING ALLERGENS PRESENT IN A PRODUCT

TECHNICAL FIELD

The present invention relates generally to product labeling, and more particularly to detecting allergens present in a product (e.g., food, cosmetics, clothing, medicine) without revealing trade secrets.

BACKGROUND

All sorts of products, ranging from food to medicine to cosmetics, have labels associated with them. Such labels, especially those for packaged food, may contain a listing of the ingredients. Concerning the example of packaged food, this listing of ingredients is important for consumers with food hypersensitivities because it helps them determine whether a food is safe for them to eat.

In 2004, the Food Allergen Labeling and Consumer Protection Act (FALCPA) was passed in the United States of America (hereinafter referred to as simply "United States" or "U.S."). This Act requires the presence of the eight major food allergens (milk, egg, fish, crustacean shellfish, tree nuts, wheat, peanuts, soybeans) in any packaged food to be declared on the ingredients list using a name that is recognizable to consumers. The FALCPA requirements only apply to foods and other products (pet foods and dietary supplements) regulated by the U. S. Food and Drug administration (FDA). However, the U.S. Department of Agriculture has adopted the FALCPA requirements for the foods which they regulate (meat products, poultry products and egg products). Also, the Tax and Trade Bureau (TTB) that regulates labeling of alcoholic beverages in the U.S. has adopted the FDA requirements. So in practice all packaged foods sold in the U.S. have to adhere to the FALCPA requirements.

While the ingredient list provides the ingredients of a packaged food, the food labeling law does not require that all ingredients need be listed if their presence does not have a function in the finished product. As a result, there may be consumers who react to a food allergen which is not one of the eight major food allergens (e.g., sesame seeds) that is not listed in the ingredients label since the food allergen does not have a function in the finished product.

Furthermore, some ingredients can be collectively labeled, such as spices, flavors and colors, which does not provide insight to the consumer. Collective terms may be used on ingredient lists if those components are not derived from the "big eight." As a result, a food ingredient which can cause a reaction in food hypersensitive consumers that is not derived from the "big eight" may be in a food without being declared on the ingredients label.

Furthermore, the ingredient list may include a listing of an unfamiliar ingredient (e.g., tahini) that is derived from an allergic food source (e.g., sesame seeds), and as a result, the consumer may be unaware of the food allergen.

Additionally, an allergen which is not an ingredient of the product may nonetheless be present in the product as a result of the manufacturing process.

Unfortunately, producers of products are not inclined to list all of the ingredients or the manufacturing process in producing the product to assist the consumers in determining whether there is an allergen present in the product since they do not want to reveal any trade secrets.

SUMMARY

In one embodiment of the present invention, a method for detecting allergens present in a product comprises receiving, by a tag associated with the product, a query containing a list of allergens to determine if an allergen is present in the product, where product information associated with the product is stored in write-only memory of the tag and where the product information can only be read internally by the tag but not externally by any device. The method further comprises determining, by a processor of the tag, if the allergen is present in the product using the list of allergens and the product information associated with the product. The method additionally comprises notifying, by the tag, a user regarding whether the allergen is present in the product based on the determination.

Other forms of the embodiment of the method described above are in a system and in a computer program product.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE DRAWINGS

A better understanding of the present invention can be obtained when the following detailed description is considered in conjunction with the following drawings, in which:

FIG. 5 is a flowchart of a method for storing product and process information of the product in secure memory on the tag in accordance with an embodiment of the present invention; and FIG. 6 is a flowchart of a method for detecting allergens present in the product in accordance with an embodiment of the present invention.

DETAILED DESCRIPTION

The present invention comprises a method, system and computer program product for detecting allergens present in a product. In one embodiment of the present invention, a tag (e.g., active RFID tag, passive RFID tag) receives a query from the user of a computing device containing a list of allergens to determine if an allergen is present in the product (e.g., product for ingestion, such as eye drops and nasal spray; a dietary product, such as food or a drink; and a wearable article, such as clothing, a watch, glasses and electronic/medical devices). The product information (e.g., list of ingredients of the product) associated with the product is stored in secure memory (e.g., write-only memory) on the tag. The tag determines if an allergen to the user is present in the product using the list of allergens in the query as well as the product information. For example, the tag may compare the list of allergens provided in the query with the list of ingredients in the product information of the product. The tag then notifies the user of the computing device regarding whether an allergen to the user is present in the product based on the determination. For example, the notification may indicate a percentage as to the likelihood that the allergen to the user is present in the product (e.g., a 20% chance that an allergic reaction could occur). In this manner, allergens are detected in a product and made known to the user without revealing the producer's trade secrets.

In the following description, numerous specific details are set forth to provide a thorough understanding of the present invention. However, it will be apparent to those skilled in the art that the present invention may be practiced without such specific details. In other instances, well-known circuits have been shown in block diagram form in order not to obscure the present invention in unnecessary detail. For the most part, details considering timing considerations and the like have been omitted inasmuch as such details are not necessary to obtain a complete understanding of the present invention and are within the skills of persons of ordinary skill in the relevant art.

Figure 1:
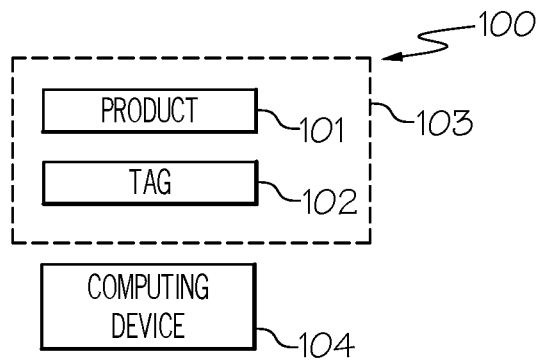
FIG. 1 illustrates a system for detecting allergens in a product in accordance with an embodiment of the present invention.

Referring now to the Figures in detail, FIG. 1 illustrates a system 100 for detecting allergens in a product 101 (e.g., product for ingestion, such as eye drops and nasal spray; a dietary product, such as food or a drink; and a wearable article, such as clothing, a watch, glasses and electronic/medical devices) in accordance with an embodiment of the present invention. System 100 includes a tag 102, such as a radio-frequency identification (RFID) tag, that is attached to product 101 or to a container of product 101 or to a store shelf nearby product 101.

In one embodiment, product 101 and tag 102 may be located at a store location 103. Store location 103 may include multiple types of display areas and fixtures for holding or displaying products within a store. Product 101 may represent a single physical item or multiple instances of a same product within a particular area, such as multiple loaves of a particular brand and type of bread.

Furthermore, in one embodiment, tag 102 stores product information pertaining to product 101. For example, tag 102 may store product information, such as the ingredients, additives, pesticides, fertilizers, etc., in the write-only memory of tag 102. The product information may also include a percentage of such ingredients, etc. (e.g., percentage by weight, volume, etc.) in product 101. By having such information not being able to be read externally by any device, the producer of the product will have less concern that trade secrets will be revealed.

In another embodiment, tag 102 stores process information pertaining to product 101. For example, tag 102 may store the process information, such as heating, cooling, frying, etc., involved in producing product 101. Such information may also be stored in the write-only memory of tag 102 so that such information will not be able to be read externally by any device thereby ensuring that the producer's trade secrets will not be revealed.

A description of tag 102 being an active RFID tag and a passive RFID tag is provided below in connection with FIGS. 2-3.

Furthermore, system 100 includes a user's computing device 104 for querying tag 102 to determine if an allergen to the user is present in product 101 as discussed further below. Computing device 104 may be any type of computing device (e.g., portable computing unit, Personal Digital Assistant (PDA), smartphone, laptop computer, mobile phone, Internet appliance and the like) configured with the capability of querying tag 102 and capturing data from tag 102. A description of computing device 104 is provided below in connection with FIG. 4.

System 100 is not to be limited in scope to any one particular architecture. System 100 may include any number of products 101, tags 102 and computing devices 104.

Figure 2:
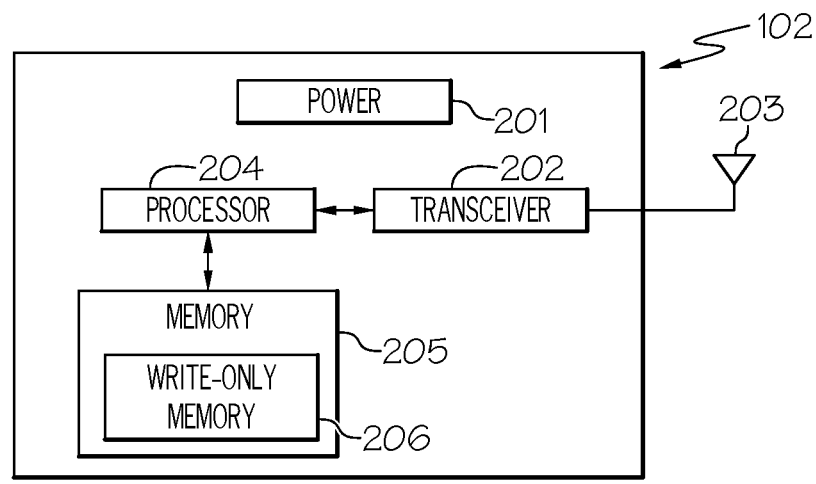
FIG. 2 is a block diagram of an active RFID tag in accordance with an embodiment of the present invention.

Referring now to FIG. 2 in conjunction with FIG. 1, FIG. 2 is a block diagram of an active RFID tag 102 in accordance with an embodiment of the present invention. Active RFID tag 102 includes a power source 201 (e.g., Lithium-Ion battery), an electronic transceiver circuitry 202, an antenna 203, a processor 204 and memory 205.

In one embodiment, transceiver 202 includes a transmitter and a receiver coupled to antenna 203 to transmit and receive radio frequency (RF) signals.

In one embodiment, memory 205 includes a write-only memory portion 206 where data can be written to but not read externally by any device. That is, data can only be read internally by tag 102 but not externally by any device once tag 102 is programmed. In one embodiment, such data may include product and process information about product 101 which may contain trade secret information that the producer of product 101 does not want to be revealed. In one embodiment, write-only memory 206 is separate from memory 205.

In one embodiment, an application for detecting allergens present in product 101, as discussed below in connection with FIGS. 5-6, is loaded into memory 205 for execution by processor 204.

Figure 3:
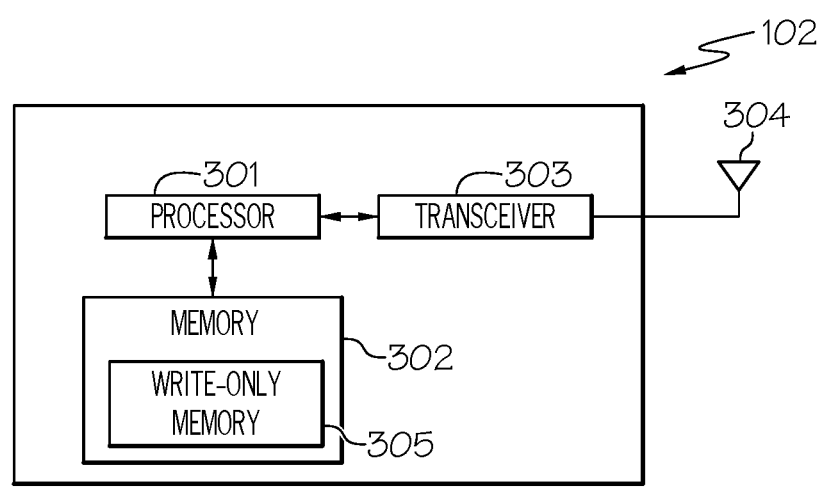
FIG. 3 is a block diagram of a passive RFID tag in accordance with an embodiment of the present invention.

Referring now to FIG. 3 in conjunction with FIG. 1, FIG. 3 is a block diagram of a passive RFID tag 102 in accordance with an embodiment of the present invention. Passive RFID tag 102 includes a processor 301, a memory 302, a transceiver 303 and an antenna 304. A power source is not used by a passive RFID tag as it collects energy from a nearby RFID reader's interrogating radio waves.

In one embodiment, transceiver 303 includes a transmitter and a receiver coupled to antenna 304 to transmit and receive radio frequency (RF) signals.

In one embodiment, memory 302 includes a write-only memory portion 305 where data can be written to but not read externally by any device. That is, data can only be read internally by tag 102 but not externally by any device once tag 102 is programmed. In one embodiment, such data may include product and process information about product 101 which may contain trade secret information that the producer of product 101 does not want to be revealed. In one embodiment, write-only memory 305 is separate from memory 302.

In one embodiment, an application for detecting allergens present in product 101, as discussed below in connection with FIGS. 5-6, is loaded into memory 302 for execution by processor 301. As previously indicated, passive RFID tag 102 does not require a battery for transmission since generally it is powered by the reader using an induction mechanism (an electromagnetic field is emitted by the reader antenna and received by the antenna, such as antenna 304, localized on passive RFID tag 102). This power may be used by passive RFID tag 102 to invoke the application for detecting allergens present in product 101, as discussed below in connection with FIGS. 5-6, to be executed by processor 301.

Figure 4:
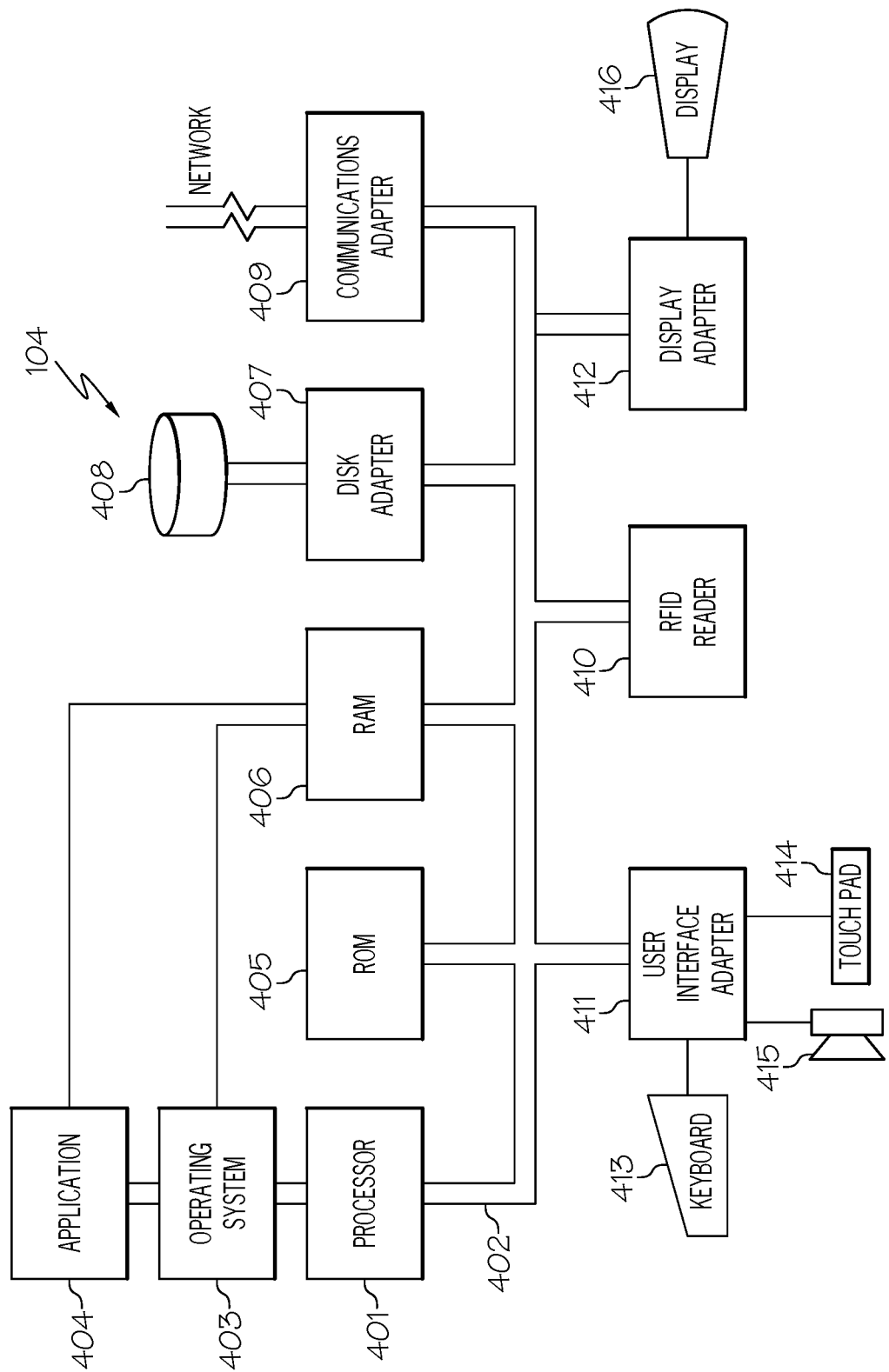
FIG. 4 illustrates a hardware configuration of a computing device which is representative of a hardware environment for practicing the present invention.

Referring now to FIG. 4, FIG. 4 illustrates a hardware configuration of computing device 104 (FIG. 1) which is representative of a hardware environment for practicing the present invention. Referring to FIG. 4, computing device 104 has a processor 401 coupled to various other components by system bus 402. An operating system 403 runs on processor 401 and provides control and coordinates the functions of the various components of FIG. 4. An application 404 in accordance with the principles of the present invention runs in conjunction with operating system 403 and provides calls to operating system 403 where the calls implement the various functions or services to be performed by application 404. Application 404 may include, for example, a program for querying tag 102 (FIG. 1) to determine if an allergen is present in product 101 (FIG. 1) as discussed further below in association with FIGS. 5-6.

Referring again to FIG. 4, read-only memory ("ROM") 405 is coupled to system bus 402 and includes a basic input/output system ("BIOS") that controls certain basic functions of computing device 104. Random access memory ("RAM") 406 and disk adapter 407 are also coupled to system bus 402. It should be noted that software components including operating system 403 and application 404 may be loaded into RAM 406, which may be computing device's 104 main memory for execution. Disk adapter 407 may be an integrated drive electronics ("IDE") adapter that communicates with a disk unit 408, e.g., disk drive. It is noted that the program for querying tag 102 to determine if an allergen is present in product 101, as discussed further below in association with FIGS. 5-6, may reside in disk unit 408 or in application 404.

Computing device 104 may further include a communications adapter 409 coupled to bus 402. Communications adapter 409 interconnects bus 402 with an outside network thereby enabling computing device 104 to communicate with other similar devices.

Computing device 104 may further include a Radio-Frequency Identification ("RFID") reader 410 configured to transmit an encoded radio signal to interrogate electronic tag 102.

I/O devices may also be connected to computing device 104 via a user interface adapter 411 and a display adapter 412. Keyboard 413, touchpad 414 and speaker 415 may all be interconnected to bus 402 through user interface adapter 411. A display monitor 416 may be connected to system bus 402 by display adapter 412. In this manner, a user is capable of inputting to computing device 104 through keyboard 413 or touchpad 414 and receiving output from computing device 104 via display 416 or speaker 415. Other input mechanisms may be used to input data to computing device 104 that are not shown in FIG. 4, such as display 416 having touch-screen capability and keyboard 413 being a virtual keyboard. Computing device 104 of FIG. 4 is not to be limited in scope to the elements depicted in FIG. 4 and may include fewer or additional elements than depicted in FIG. 4.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As stated in the Background section, while the ingredient list provides the ingredients of a packaged food, the food labeling law does not require that all ingredients need be listed if their presence does not have a function in the finished product. As a result, there may be consumers who react to a food allergen which is not one of the eight major food allergens (e.g., sesame seeds) that is not listed in the ingredients label since the food allergen does not have a function in the finished product. Furthermore, some ingredients can be collectively labeled, such as spices, flavors and colors, which does not provide insight to the consumer. Collective terms may be used on ingredient lists if those components are not derived from the "big eight." As a result, a food ingredient which can cause a reaction in food hypersensitive consumers that is not derived from the "big eight" may be in a food without being declared on the ingredients label. Furthermore, the ingredient list may include a listing of an unfamiliar ingredient (e.g., tahini) that is derived from an allergic food source (e.g., sesame seeds), and as a result, the consumer may be unaware of the food allergen. Additionally, an allergen which is not an ingredient of the product may nonetheless be present in the product as a result of the manufacturing process. Unfortunately, producers of products are not inclined to list all of the ingredients or the manufacturing process in producing the product to assist the consumers in determining whether there is an allergen present in the product since they do not want to reveal any trade secrets.

The principles of the present invention provide a means for detecting allergens present in a product (e.g., product for ingestion, such as eye drops and nasal spray; a dietary product, such as food or a drink; and a wearable article, such as clothing, a watch, glasses and electronic/medical devices) without revealing the producer's trade secrets as discussed below in connection with FIGS. 5-6. FIG. 5 is a flowchart of a method for storing product and process information of product 101 (FIG. 1) in secure memory on tag 102 (FIGS. 1-3). FIG. 6 is a flowchart of a method for detecting allergens present in product 101.

As stated above, FIG. 5 is a flowchart of a method 500 for storing product and process information of product 101 (FIG. 1) in secure memory (e.g., write-only memory 206, 305 of FIGS. 2 and 3, respectively) on tag 102 (FIGS. 1-3) in accordance with an embodiment of the present invention.

Referring to FIG. 5, in conjunction with FIGS. 1-4, in step 501, product information, such as the ingredients, additives, pesticides, fertilizers, etc., is stored in secure memory (e.g., write-only memory 206, 305) on tag 102. The product information may also include a percentage of such ingredients, etc. (e.g., percentage by weight, volume, etc.) in product 101. In one embodiment, such information is encoded in write-only memory 206, 305 of tag 102. By having such information only being able to be read internally by tag 102 but not externally by any device once tag 102 is programmed, the producer of product 101 will have less concern that trade secrets will be revealed. Furthermore, such information may be used by tag 102 to determine if an allergen to the user of computing device 104 is present in product 101 as discussed below in connection with FIG. 6.

In step 502, process information, such as heating, cooling, frying, etc., involved in producing product 101 is stored in secure memory (e.g., write-only memory 206, 305) on tag 102. In one embodiment, such information is encoded in write-only memory 206, 305 of tag 102. By having such information only being able to be read internally by tag 102 but not externally by any device once tag 102 is programmed, the producer of product 101 will have less concern that trade secrets will be revealed. Furthermore, such information may be used by tag 102 to determine if an allergen to the user of computing device 104 is present in product 101 as discussed below in connection with FIG. 6.

FIG. 6 is a flowchart of a method 600 for detecting allergens present in product 101 (FIG. 1) in accordance with an embodiment of the present invention.

Referring to FIG. 6, in conjunction with FIGS. 1-5, in step 601, tag 102 receives a query from the user of computing device 104 containing a list of allergens and a non-mutable identifier to determine if an allergen is present in product 101. In one embodiment, computing device 104 may store a list of known allergens to the user, such as in a storage device (e.g., memory 405, disk unit 408). Furthermore, in one embodiment, computing device 104 may store a non-mutable identifier, such as the media access control address (MAC address), the international mobile station equipment identity (IMEI), a phone number, a public key, etc., that is associated with the user of computing device 104. As will be discussed further below, such an identifier may be used by tag 102 to determine if the user is "fishing" for ingredients of product 101. When a number of queries associated with the same identifier exceeds a threshold number of queries over a period of time, tag 102 will no longer determine whether an allergen to the user is present in product 101.

In step 602, a determination is made by tag 102 as to whether the number of queries associated with the non-mutable identifier exceeds the threshold number of queries over a period of time. If the number of queries associated with the non-mutable identifier exceeds the threshold number of queries over the period of time, then the user may be engaged in an attempt to obtain the ingredients of product 101. In such a situation, in an attempt to prevent the disclosure of the producer's trade secrets, tag 102, in step 603, notifies the user of computing device 104 that the user exceeded the maximum number of queries.

In one embodiment, in the situation where the user of computing device 104 submits multiple queries to tag 102, tag 102 may analyze the behavioral pattern of the queries to determine if the user is engaging in an attempt to obtain the ingredients of product 101. If the behavioral pattern suggests that the user is engaging in an attempt to obtain the ingredients of product 101, then tag 102 may notify the user of computing device 104 that tag 102 will not be able to determine if an allergen to the user is present in product 101 in order to prevent the disclosure of the producer's trade secrets.

Returning to step 602 of FIG. 6, if, however, the number of queries associated with the non-mutable identifier does not exceed the threshold number of queries over the period of time, then, in step 604, tag 102 determines if an allergen to the user is present in product 101 using the list of allergens in the query as well as the product and process information (stored in write-only memory 206, 305 which is accessible only by tag 102) associated with product 101. For example, tag 102 may compare the list of allergens provided in the query with the list of ingredients in the product information of product 101. If there is a match, then tag 102 has detected an allergen to the user that is present in product 101. In another example, tag 102 may utilize the manufacturing process information to determine if an allergen listed in the list of allergens provided in the query will be present in product 101. In a further example, tag 102 may utilize the product and process information of product 101 to determine if a mixture of ingredients utilizing the manufacturing process will result in the presence of an allergen listed in the list of allergens provided in the query.

In step 605, tag 102 notifies the user of computing device 104 regarding whether an allergen to the user is present in product 101 based on the determination of step 604. The notification may include an indication that an allergen to the user is present in product 101, an indication that an allergen to the user is likely to be present in product 101 or an indication that there is no presence of an allergen to the user in product 101. Furthermore, in one embodiment, the notification may include a percentage as to the likelihood of the allergen being present in product 101. For example, the notification may indicate that there is a 20% chance that a particular allergen listed in the list of allergens provided in the query is present in product 101.

In this manner, allergens are detected in a product (e.g., product for ingestion, such as eye drops and nasal spray; a dietary product, such as food or a drink; and a wearable article, such as clothing, a watch, glasses and electronic/medical devices) and made known to the user without revealing the producer's trade secrets.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for detecting allergens present in a product, the method comprising:
   receiving, by a tag associated with said product, a query containing a list of allergens to determine if an allergen is present in said product, wherein product information associated with said product is stored in a memory of said tag, wherein said product information can only be read internally by said tag but not externally by any device;
   determining, by a processor of said tag, if said allergen is present in said product using said list of allergens and said product information associated with said product; and
   notifying, by said tag, a computing device of a user regarding whether said allergen is present in said product based on said determination.

2. The method as recited in claim 1, wherein process information associated with said product is stored in said memory of said tag, wherein said process information can only be read internally by said tag but not externally by any device.

3. The method as recited in claim 2 further comprising:
   determining if said allergen is present in said product using said list of allergens, said product information associated with said product and said process information associated with said product.

4. The method as recited in claim 1, wherein said query comprises a non-mutable identifier.

5. The method as recited in claim 4 further comprising:
   notifying said computing device of said user that said user has exceeded a maximum number of queries in response to a number of queries associated with said non-mutable identifier exceeding a threshold number of times over a period of time.

6. The method as recited in claim 1, wherein said notification indicates one of the following: presence of said allergen in said product, a likely presence of said allergen in said product, and no presence of said allergen in said product.

7. The method as recited in claim 1, wherein said tag is attached to one of the following: said product, a container of said product and a store shelf.

8. The method as recited in claim 1, wherein said product is selected from the group consisting of a product for ingestion, a dietary product and a wearable article.

9. A computer program product for detecting allergens present in a product, the computer program product comprising a computer readable storage medium having program code embodied therewith, the program code comprising the programming instructions for:
   receiving, by a tag associated with said product, a query containing a list of allergens to determine if an allergen is present in said product, wherein product information associated with said product is stored in a memory of said tag, wherein said product information can only be read internally by said tag but not externally by any device;
   determining if said allergen is present in said product using said list of allergens and said product information associated with said product; and notifying, by said tag, a computing device of a user regarding whether said allergen is present in said product based on said determination.

10. The computer program product as recited in claim 9, wherein process information associated with said product is stored in said memory of said tag, wherein said process information can only be read internally by said tag but not externally by any device.

11. The computer program product as recited in claim 10, wherein the program code further comprises the programming instructions for:
   determining if said allergen is present in said product using said list of allergens, said product information associated with said product and said process information associated with said product.

12. The computer program product as recited in claim 9, wherein said query comprises a non-mutable identifier.

13. The computer program product as recited in claim 12, wherein the program code further comprises the programming instructions for:
   notifying said computing device of said user that said user has exceeded a maximum number of queries in response to a number of queries associated with said non-mutable identifier exceeding a threshold number of times over a period of time.

14. The computer program product as recited in claim 9, wherein said notification indicates one of the following: presence of said allergen in said product, a likely presence of said allergen in said product, and no presence of said allergen in said product.

15. The computer program product as recited in claim 9, wherein said tag is attached to one of the following: said product, a container of said product and a store shelf.

16. The computer program product as recited in claim 9, wherein said product is selected from the group consisting of a product for ingestion, a dietary product and a wearable article.

17. A tag, comprising:
   a memory unit for storing a computer program for detecting allergens present in a product; and
   a processor coupled to the memory unit, wherein the processor is configured to execute the program instructions of the computer program comprising:
      receiving a query containing a list of allergens to determine if an allergen is present in said product, wherein product information associated with said product is stored in a memory of said tag, wherein said product information can only be read internally by said tag but not externally by any device;
      determining if said allergen is present in said product using said list of allergens and said product information associated with said product; and
      notifying a computing device of a user regarding whether said allergen is present in said product based on said determination.

18. The tag as recited in claim 17, wherein process information associated with said product is stored in said memory of said tag, wherein said process information can only be read internally by said tag but not externally by any device.

19. The tag as recited in claim 18, wherein the program instructions of the computer program further comprise:
   determining if said allergen is present in said product using said list of allergens, said product information associated with said product and said process information associated with said product.

20. The tag as recited in claim 17, wherein said query comprises a non-mutable identifier, wherein the program instructions of the computer program further comprise:
   notifying said computing device of said user that said user has exceeded a maximum number of queries in response to a number of queries associated with said non-mutable identifier exceeding a threshold number of times over a period of time.

* * * * *